United States Patent [19]

Parnell

[11] Patent Number: 5,051,426

[45] Date of Patent: Sep. 24, 1991

[54] METHOD FOR EFFECTING WITHDRAWAL FROM DRUG DEPENDENCY

[75] Inventor: Francis W. Parnell, Ross, Calif.

[73] Assignee: Parnell Pharmaceuticals, Inc., San Rafael, Calif.

[21] Appl. No.: 500,034

[22] Filed: Mar. 27, 1990

[51] Int. Cl.$^5$ ............................................. A61K 31/52
[52] U.S. Cl. .................................. 514/263; 514/812; 514/811; 514/813
[58] Field of Search ................ 514/263, 811, 812, 813

[56] References Cited

U.S. PATENT DOCUMENTS

| | | | |
|---|---|---|---|
| 3,598,824 | 8/1971 | Troxler et al. | 260/256.4 |
| 3,706,831 | 12/1972 | Plotnikoff | 424/153 |
| 4,117,161 | 9/1978 | Pozuelo | 424/319 |
| 4,124,715 | 11/1978 | Pozuelo | 424/266 |
| 4,165,376 | 8/1979 | Rosenberg | 424/267 |
| 4,276,890 | 7/1981 | Fichera | 424/48 |
| 4,325,952 | 4/1982 | Silvestrini et al. | 424/250 |
| 4,696,818 | 9/1987 | Kim | 424/195.1 |
| 4,778,677 | 10/1988 | Ebbesen | 424/128 |
| 4,786,653 | 11/1988 | Golwyn | 514/654 |
| 4,788,189 | 11/1988 | Glazer | 514/221 |

OTHER PUBLICATIONS

Dole, (1988) *Journal of the American Medical Association* 260 (20):3025–3029.
Nencini et al., (1988) *Psychopharmacology* 96:40–44.
Schechter et al., (1988) *Pharmacol. Biochem. and Behavior* 30:1089–1092.
Benowitz, (1988) *The New England Journal of Medicine* 319(20):1318–1330.

*Primary Examiner*—Frederick E. Waddell
*Assistant Examiner*—Diane Gardner
*Attorney, Agent, or Firm*—Dianne E. Reed

[57] ABSTRACT

Methods and compositions are provided for treating drug-dependent individuals so as to effect withdrawal from the drug of abuse, e.g., natural and synthetic narcotics, or stimulant-type drugs such as cocaine, amphetamines, nicotine, or the like. The method involves substitution therapy wherein a serotonin antagonist such as ergotamine or a derivative thereof and a CNS stimulant such as caffeine are substituted for the drug of abuse.

29 Claims, 5 Drawing Sheets

METHOD FOR EFFECTING WITHDRAWAL FROM DRUG DEPENDENCY

TECHNICAL FIELD

The present invention relates generally to treatment of persons during withdrawal from drug dependency, and more particularly relates to compositions and methods for treating withdrawal from dependency on any one of a variety of different types of drugs, e.g., cocaine, amphetamines, nicotine, natural and synthetic narcotics, and other addictive agents.

BACKGROUND

It is common knowledge that there are many individuals who become addicted to certain types of drugs taken either for medical reasons or for "recreational", non-medical use. Addiction, as has been defined by the Drug Addiction Committee of the National Research Council, is a state of periodic or chronic intoxication detrimental to the individual and produced by the repeated administration of a drug. Thus, an "addictive drug" as used herein is one that is initially used for any one of a number of purposes, e.g., for the relief of physical or psychic pain, and which if used consistently leads to dependency on the part of the individual taking the drug. The addicted individual develops a continuing craving for the drug and experiences withdrawal symptoms if an attempt is made to discontinue drug use.

Various pharmacological approaches for treating drug dependence have been tried. These approaches have typically involved attempts at treating the craving for the abused drug or alleviating the symptoms of withdrawal. While some of the approaches tried have been successful in varying degrees, each has presented certain limitations and drawbacks. For example, withdrawal symptoms may be only minimally relieved upon treatment, leading to an enhanced craving for the problem drug. Or, in substitution therapy, the "substituted" drug may not adequately mimic the psychic and physiological effects obtained with the abused drug, and the addict may quickly return to use of that drug. Finally, the drug used in treatment may itself create problems with dependency and withdrawal.

Thus, a very substantial need in the art exists for a therapeutic method of treating drug abuse such that a drug-addicted individual is readily able to discontinue use of an abused drug without encountering the above-mentioned problems.

CITATION OF RELATED REFERENCES

The following references relate to methods and compositions for treating drug addiction and/or symptoms of withdrawal from drug dependency.

Administration of "incompatible" drugs to treat addiction: U.S. Pat. No. 4,786,653 to Golwyn relates to the administration of phenelzine or an equivalent phenylalkylhydrazine, substances that are physiologically incompatible with addictive drugs such as amphetamines and cocaine. U.S. Pat. Nos. 1,796,977 and 1,782,111 describe the preparation of disulfiram ("Antabuse"), an alcohol deterrent.

Treatment of drug withdrawal, generally, including withdrawal from narcotics and amphetamines: U.S. Pat. No. 4,696,818 to Kim relates to a method for alleviating symptoms associated with a variety of drugs, the method comprising administering an herbal composition to the drug dependent individual. U.S. Pat. No. 3,706,831 to Plotnikoff also describes a method for treating addiction to any one of a number of different types of drugs, which method involves administering to the addict a composition containing 2-imino-5-phenyl-4-oxazolidinone. U.S. Pat. Nos. 4,117,161 and 4,124,715 to Pozuelo disclose methods and compositions for treating withdrawal from narcotics and amphetamines which involve administration of alpha-methyl-para-tyrosine (in the '161 patent) or fusaric acid (in the '715 patent) to the affected individual.

Treatment of nicotine withdrawal, specifically: U.S. Pat. No. 4,325,952 to Baiocchi et al describes use of a piperazine compound to treat the symptoms associated with withdrawal from nicotine. U.S. Pat. No. 4,788,189 to Glazer involves treatment of nicotine withdrawal by administration of clonidine in conjunction with a tricyclic antidepressant drug. U.S. Pat. No. 4,276,890 to Fichera describes a composition for alleviating symptoms of nicotine withdrawal by administering to the affected individual a composition containing a gamma pyrone such as maltol or ethyl maltol. U.S. Pat. No. 3,598,824 to Bormann discloses the use of 7H-pyrrolo-2,3-D-pyrimidine-5-acetimidates for treating nicotine withdrawal.

Physiological mechanism of addiction: Dole, *Journal of the American Medical Association* 260(20): 3025–3029 (25 November 1988) presents an analysis of the frequent failure of methadone treatment to cure narcotic-addicted individuals. P. Nencini et al., *Psychopharmacology* 96:40–44 (1988), studied the effect of a calcium channel blocker (nimodipine) on the discriminative stimulus properties of d-amphetamine. M. D. Schechter et al., *Pharmacol. Biochem. and Behavior* 30:1089–1092 (1988), also studied the mechanism of amphetamine addiction (as well as the physiological effect of a synthetic benzothiadiazepine—"CGS 10746B"—on amphetamine addiction). N. Benowitz, *The New England Journal of Medicine* 319(20):1318–1330, examines the pharmacology of nicotine and nicotine addiction and summarizes efforts at nicotine-substitution therapy.

SUMMARY OF THE INVENTION

Accordingly, it is a primary object of the present invention to overcome the above-mentioned disadvantages of the prior art, and to provide a method of treating a drug-addicted individual so as to effect withdrawal from the drug dependency.

It is another object of the invention to provide such a method which involves administering therapeutically effective amounts of a serotonin antagonist and a central nervous system ("CNS") stimulant.

It is still another object of the invention to provide such a method which involves administering the serotonin antagonist and CNS stimulant, simultaneously, in a single composition.

It is yet another object of the invention to provide such a method in which the composition is administered as a substitute for the abused drug in decreasing dosage units over a predetermined treatment period.

It is a further object of the invention to provide such a method wherein the composition is administered transmucosally.

It is yet a further object of the invention to provide such a method wherein the composition is administered either orally or parenterally.

It is still a further object of the invention to provide a composition for use in the aforementioned treatment methods.

It is another object of the invention to provide such a composition in which the serotonin antagonist is ergotamine, an ergotamine derivative, or a pharmacologically acceptable salt thereof, and the CNS stimulant is xanthine, a xanthine derivative, or a pharmacologically acceptable salt thereof.

Additional objects, advantages and novel features of the invention will be set forth in part in the description which follows, and in part will become apparent to those skilled in the art upon examination of the following, or may be learned by practice of the invention.

In one aspect of the invention, an addicted individual who is attempting to discontinue use of an abused drug is treated by administration of a serotonin antagonist and a CNS stimulant as will be defined herein. It has now been surprisingly discovered by the inventors herein that these two types of compounds work synergistically to substantially eliminate the physiological withdrawal symptoms typically associated with withdrawal from cocaine, amphetamines, nicotine, natural and synthetic narcotics, and other addictive agents, as well as significantly reducing the addicted individual's craving for the drug of abuse.

It is preferred that the two types of compounds be administered in a single composition, as a substitute for the drug of abuse, over a predetermined treatment period. In order that the individual withdraw from the compounds described herein as well as from the drug of abuse, the serotonin antagonist and CNS stimulant, the compounds and compositions described herein are preferably administered in decreasing unit dosage amounts.

In another aspect of the invention, a composition is provided for use in the treatment method, the composition containing the serotonin antagonist, the CNS stimulant and, preferably, one or more pharmacologically acceptable excipients.

DETAILED DESCRIPTION OF THE INVENTION

Figure 1:
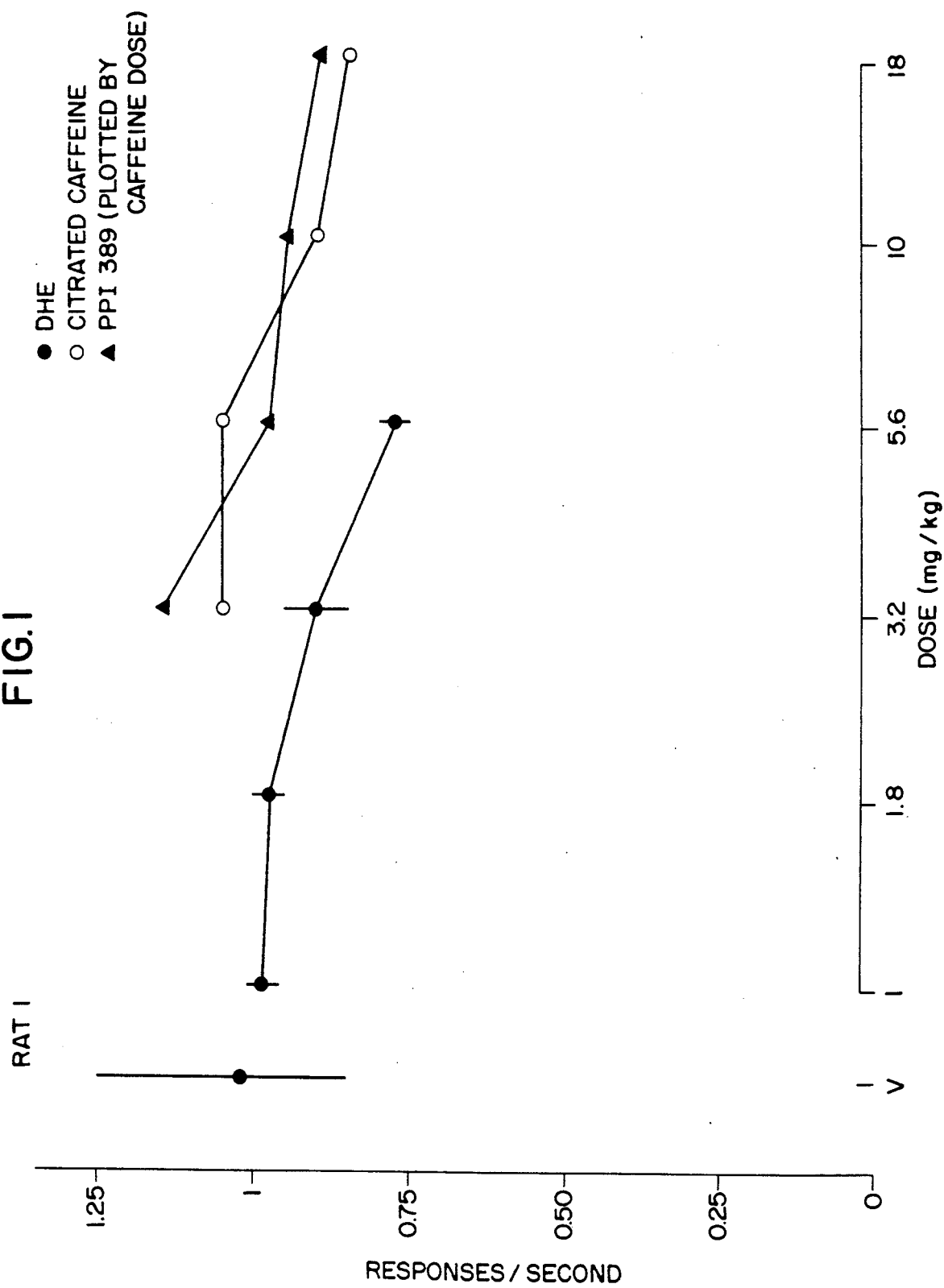
FIGS. 1 through 5 are dose-response curves corresponding to the experimental work summarized in Example 1.

Definitions:

Before the present method of effecting withdrawal from drug addiction is disclosed and described, it is to be understood that this invention is not limited to the specifically identified components or modes of administration disclosed herein, as such components or modes of administration may, of course, vary. It is also to be understood that the terminology used herein is used for purpose of describing particular embodiments only and is not intended to be limiting.

It must be noted that as used in this specification and the appended claims, the singular forms "a", "an" and "the" include plural reference unless the context clearly dictates otherwise. Thus, for example, reference to "an ergotamine derivative" or to "a xanthine derivative" includes mixtures of such compounds and their pharmaceutically acceptable salts, while reference to the "method of treatment" or to the "mode of administration" will include one or more different methods of treatment and administration known to those skilled in the art or which will become known to those skilled in the art upon reading this disclosure.

The term "serotonin antagonist" as used herein is used in its conventional sense to indicate a compound which is effective to inhibit the action of serotonin (5-hydroxytryptamine, or "5-HT").

The term "CNS stimulant" as used herein is also used in its conventional sense to indicate a compound which exerts its action through nonselective excitation of the central nervous system.

The term "lower alkyl" as used herein in the description of chemical structures is intended to encompass alkyl groups having 1 through 6, preferably 1 through 4, carbon atoms, e.g., methyl, ethyl, propyl, t-butyl, n-hexyl, and the like.

The Compounds and Compositions of the Invention:

The present method involves administering to a drug-addicted individual a first compound which is a serotonin antagonist in conjunction with a second compound which is a CNS stimulant. The compounds are preferably administered as a single composition, although they may be administered separately so long as they are administered within a narrow enough window of time to ensure presence of both compounds in the individual's circulation at the same time.

The serotonin antagonist is preferably ergotamine, an ergotamine derivative, or a pharmacologically acceptable salt thereof. Preferred ergotamine derivatives are those identified in A. Korolkovas, *Essentials of Medicinal Chemistry*, 2nd Ed. (New york: Wiley-Interscience, 1988), at page 322: acetergamine, brazergoline, bromerguride, cianergoline, delorgotrile, dihydroergotamine mesylate, disulergine, ergonovine maleate, ergotamine tartrate, etisulergine, lergotrile, lysergide, mesulergine, metergoline, metergotamine, methylergonovine maleate, methysergide maleate, nicergoline, pergolide mesylate, propisergide, proterguride and terguride. The ergotamine compound used herein should be chemically and physically stable with respect to other components of the composition and should be soluble in the vehicle selected for drug administration. A particularly preferred serotonin antagonist for use herein is dihydroergotamine ("DHE"), and the more preferred form of this compound is its mesylate salt ("DHE mesylate"). The use of acid addition salts other than the mesylate is within the scope of the present invention as well, as will be described below.

The CNS stimulant is preferably one that has the structural formula:

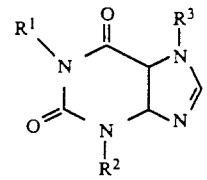

wherein $R^1$, $R^2$ and $R^3$ are independently selected from the group consisting of hydrogen and lower alkyl. Included within this structural formula are caffeine, theophylline and theobromine. A preferred compound within this group is caffeine, and the preferred form for use herein is the citrate salt (caffeine citrate).

While dihydroergotamine mesylate and caffeine citrate exemplify a preferred embodiment of the invention, other pharmacologically acceptable acid addition salts are also within the scope of the present invention.

Such salts are those which retain the biological effectiveness and properties of the free bases and which are not biologically or otherwise undesirable. These salts may be formed with inorganic acids such as hydrochloric acid, hydrobromic acid, sulfuric acid, nitric acid, phosphoric acid or the like, or with organic acids such as acetic acid, propionic acid, glycolic acid, pyruvic acid, oxalic acid, malic acid, malonic acid, succinic acid, maleic acid, fumaric acid, tartaric acid, benzoic acid, cinnamic acid, mandelic acid, methanesulfonic acid, ethanesulfonic acid, p-toluenesulfonic acid, salicylic acid and the like.

The compositions will also generally include carriers, vehicles, adjuvants, excipients or the like, depending on the form of the composition (i.e., solid, liquid, etc.), as well as on the intended mode of administration.

In addition, depending on the intended mode of administration, the compositions used may be in the form of solid, semi-solid or liquid dosage forms, such as, for example, tablets, suppositories, pills, capsules, powders, liquids, suspensions, or the like, preferably in unit dosage forms suitable for single administration of precise dosages.

Utility and Mode of Administration:

As noted above, the method of the invention is intended to enable a drug-addicted individual to discontinue use of an abused drug without experiencing intense craving for that drug or severe physiological withdrawal symptoms.

The present invention is useful for effecting withdrawal from a wide range of drugs possessing addictive properties. The compositions of the invention are, for example, useful in treating an individual withdrawing from narcotics, e.g., from the use of opium alkaloids such as morphine, heroin and codeine, or from synthetic non-opiate narcotics such as meperidine and methadone. The present compositions are also useful for treating an individual who is addicted to stimulant-type drugs such as cocaine, amphetamines, and nicotine, or who has abused lysergic acid diethylamide (LSD).

It is intended that the selected serotonin antagonist and CNS stimulant as described in the preceding section be administered as a substitute for the abused drug. Thus, at the beginning of the treatment period, the aforementioned compounds will be administered in an amount effective to achieve as nearly as possible the psychic and physiological effects experienced with the drug of abuse, with the amount of the compounds administered gradually decreased over the treatment period. Typically, this will involve administration of a therapeutically effective amount of a composition containing the compounds at least once every twenty-four hours. By "therapeutically effective amount" is intended a dosage quantity effective to significantly alleviate craving for the drug of abuse as well as reducing the intensity of or eliminating withdrawal symptoms associated with its discontinuance. The total treatment period will normally be at least about two weeks, preferably at least about four weeks, and possibly much longer, e.g., up to a year or more, if psychic withdrawal symptoms persist.

The amount of serotonin antagonist and CNS stimulant administered will, of course, be dependent on the subject being treated, the severity of the addiction, the manner of administration and the judgment of the prescribing physician. However, an effective dosing regimen will at the outset generally involve daily administration of a composition containing about 1 to 10, more preferably 2 to 6 mg serotonin antagonist and about 2 to 12, more preferably 6 to 10 mg CNS stimulant. For example, an optimal regimen for parenteral administration will involve daily injection of 1 ml of an aqueous composition containing 4 mg/ml dihydroergotamine mesylate and 8 mg/ml citrated caffeine. Gradual reduction in dosage throughout the treatment period is clearly desirable. The length of the "tail-off" period will vary, clearly, with the individual undergoing treatment, the drug of abuse, the severity of the affliction, and the like. Reduction in dosage will generally not be initiated prior to two weeks into the treatment period.

Administration of the compounds described herein can be via any of the accepted modes of administration for therapeutic agents. These methods include oral, rectal, parenteral, transdermal, transmucosal, subcutaneous and other systemic modes. The preferred methods of administration are parenteral and transmucosal.

For solid compositions, e.g., for oral administration, the compounds will be formulated with, e.g., pharmaceutical grades of mannitol, lactose, starch, magnesium stearate, sodium saccharin, talc, cellulose, glucose, sucrose, magnesium carbonate, or the like. The compositions may also be formulated as suppositories using, for example, polyalkylene glycols (e.g., propylene glycol) as the carrier. Liquid pharmaceutically administerable compositions can be prepared by dissolving, dispersing, etc., the serotonin antagonist and CNS stimulant as described hereinabove and optional pharmaceutical adjuvants in an excipient such as, for example, water, saline, aqueous dextrose, glycerol, ethanol, or the like, to thereby form a solution or suspension. If desired, the pharmaceutical composition to be administered may also contain minor amounts of nontoxic auxiliary substances such as wetting or emulsifying agents, pH buffering agents or the like, e.g., sodium acetate, sorbitan monolaurate, triethanolamine sodium acetate, triethanolamine oleate, etc. Actual methods of preparing such dosage forms are known in the art, or will be apparent, to those skilled in the art; for example, see *Remington's Pharmaceutical Sciences,* Mack Publishing Co., Easton, Pennsylvania.

For oral administration, specifically, a pharmaceutically acceptable non-toxic composition is generally formed by the incorporation of any of the normally employed excipients described above. Such compositions can take the form of solutions, suspensions, tablets, pills, capsules, powders, sustained release formulations and the like. Such compositions can contain 1 wt.% to 95 wt.% active ingredients, preferably 1 wt.% to 70 wt.%.

Parenteral administration is generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients include, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, or the like.

A more recent approach for parenteral administration employs the implantation of a slow-release or sustained-release system, such that an approximately constant level of dosage is maintained. See, e.g., U.S. Pat.

No. 3,710,795, the disclosure of which is incorporated by reference herein.

The compounds of the invention may also be delivered through the body surface, i.e., transdermally or transmucosally. By "transdermal" as used herein is meant passage into and through the skin to achieve effective therapeutic blood levels. "Transmucosal" is intended to mean passage through a mucosal membrane of a living organism and thus includes delivery of drugs through either nasal or buccal tissue. Transdermal or transmucosal delivery will involve topical application of the compounds of the invention in the form of an ointment, gel, cream, or the like, or may involve use of a drug delivery device as taught, for example, in U.S. Pat. Nos. 3,742,951, 3,797,494, or 4,568,343. Such compositions may optionally contain a permeation enhancer as known in the art, to increase the rate at which the compounds of the invention permeate through the skin or mucosal tissue.

Transmucosal administration of the present compositions is preferably effected transnasally, and more preferably by way of a nasal spray. Preferred vehicles for use in such a nasal spray are sterile saline solutions having a pH compatible with that of the nasal mucosa, and a particularly preferred vehicle for use herein is the nasal lubricant manufactured and sold under the trademark "pretz" by Parnell Pharmaceuticals (San Rafael, California), the assignee of the present patent application. Formulation and use of a pretz ™-based composition for use herein are described in Examples 5 through 7 below.

It is to be understood that while the invention has been described in conjunction with the preferred specific embodiments thereof, that the foregoing description as well as the example which follows are intended to illustrate and not limit the scope of the invention. Other aspects, advantages and modifications within the scope of the invention will be apparent to those skilled in the art to which the invention pertains.

EXAMPLE 1

In order to investigate the ability of a composition containing 4 mg/ml dihydroergotamine mesylate and 8 mg/ml caffeine citrate (sometimes referred to herein as "PPI 389") to antagonize the discriminative stimulus and reinforcing properties of cocaine (and related compounds) it was first necessary to determine behaviorally active doses for rats. To that end, the ability of PPI 389 to alter the rate of responding for food was examined.

Experimental sessions were conducted in four identical commercially available operant conditioning chambers (Med Associates, model ENV-001; overall dimensions 8.5"×8.5"×11"). These chambers were enclosed in sound attenuating chambers. Ventilation fans, which also served to provide masking noise during sessions, were mounted on each chamber. Each chamber had two levers mounted on the front wall, equidistant from a food cup. A 28 volt stimulus light was mounted on the wall above each lever. In addition, each chamber was equipped with a pellet dispenser to provide for the delivery of 45 mg Noyes pellets. Scheduling of contingencies and data recording were accomplished by an IBM XT computer which was programmed with OPN software and connected to each chamber via a MED Associates interface.

Five experimentally naive, male Wistar-Firth rats served as subjects. They were reduced to 85% of their free-feeding weight at the start of the experiment. Throughout the experiment, food was only available during the experimental sessions, with subsequent post-session feeding as necessary to maintain their body weight. Water was always provided, ad libitum, in the home cages. All rats were shaped by the method of successive approximations to press the left lever of the chamber in order to obtain a food pellet. Following this, the number of lever presses required to produce a food pellet was increased during subsequent sessions, until all rats were responding 15 times for each pellet ("fixed ratio 15", or "FR 15"). Finally, each session was divided into eight components. The first component was 10 minutes in duration, during which time the chamber was dark and responses were recorded but had no programmed consequence ("time out", or "TO"). The next component was five minutes in duration, during which time the light over the left lever was illuminated and responding was maintained under an FR 15 schedule (i.e., every fifteenth lever press produced a food pellet). These components alternated throughout the session until each had been presented four times. Thus the schedule was a multiple time out fixed ratio (Mult TO FR). Each session, therefore, was an hour long and consisted of four TO and four FR components. When performance (responding for food) was stable, i.e, the rate of responding was consistent both within and across sessions, drug testing began.

Experimental sessions were conducted five days a week, Monday through Friday. In general, drug sessions occurred on Tuesdays and Fridays, with vehicle sessions conducted on Thursdays. Mondays and Wednesdays were baseline sessions during which no injections were given. The drugs tested were DHE mesylate (1–5.6 mg/kg), citrated caffeine (3.2–18 mg/kg) and PPI 389 (the combination as described above). All drugs were injected intraperitoneally in a volume of 1 ml/kg. Sterile water served as a vehicle. A cumulative dosing procedure was used to obtain dose-effect data. Specifically, animals were injected four times each session, at the start of each TO component. The total cumulative doses obtained were spaced by quarter log units. For example, at the start of the first TO component an animal might be injected with 1 mg/kg of drug. The effects of this dose on rate of responding would be assessed 10 minutes later during the first FR component. At the end of this FR component (the start of the second TO component) a second injection would be given. In this example the dose injected would be 0.8 mg/kg so that the cumulative dose would be 1.8 mg/kg. The effects of 1.8 mg/kg would be assessed during the next FR component. At the start of the third TO component, another injection would be given. In this example, 1.4 mg/kg of drug so that the total drug would be 3.2 mg/kg. The effects of 3.2 mg/kg would be obtained in the third FR component. Finally, at the start of the fourth TO component a final injection would be given. In this example, 2.4 mg/kg of drug so that the total dose would be 5.6 mg/kg. The effects of 5.6 mg/kg would be obtained in the fourth and final FR component. Drug data are compared to sessions during which animals are injected with vehicle at the start of each TO component. A given dose of a drug is said to have an effect to the extent that the drug data for an individual animal fall outside the range of the vehicle data obtained for that animal.

Figure 2:
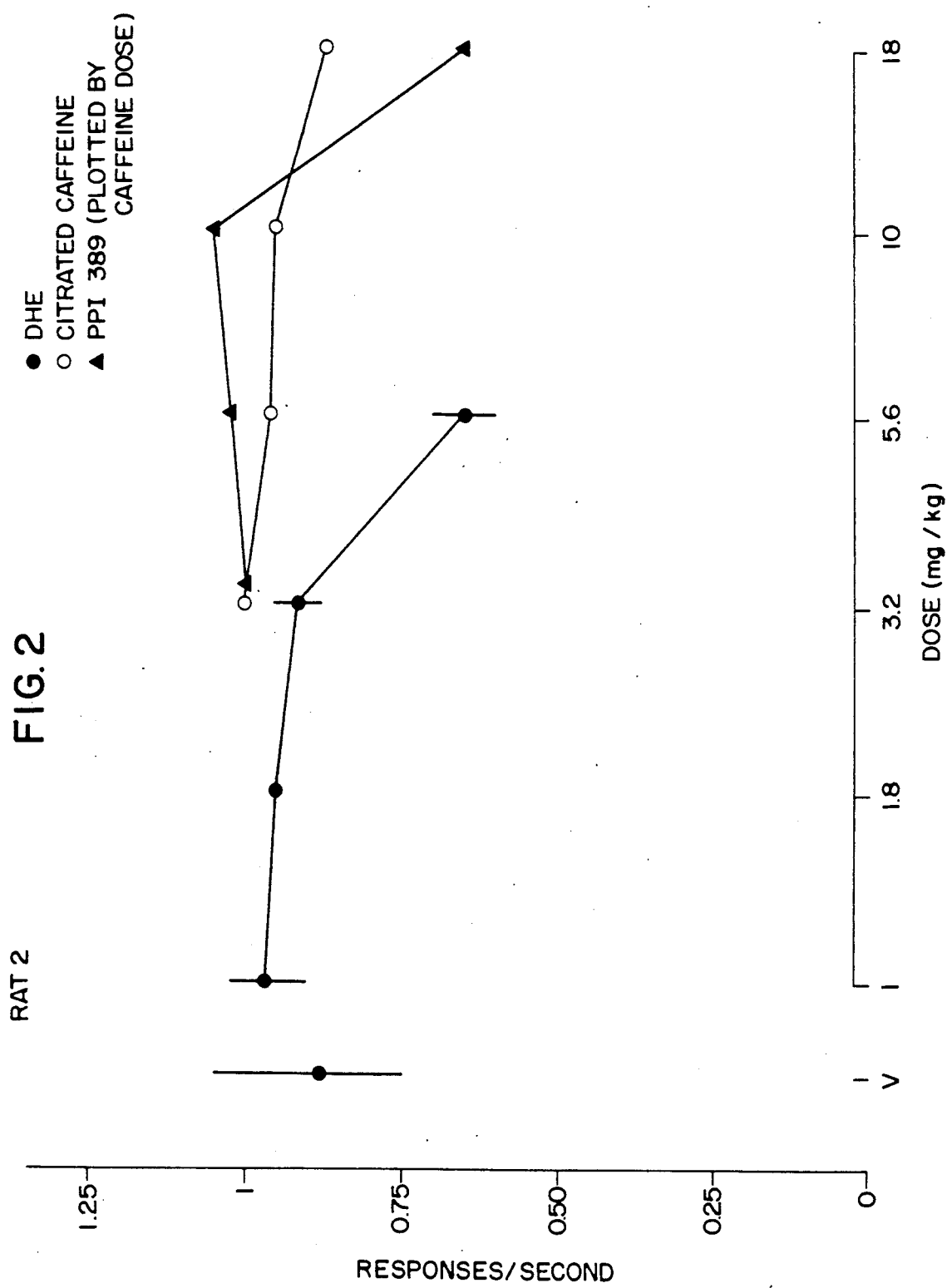
Figure 3:
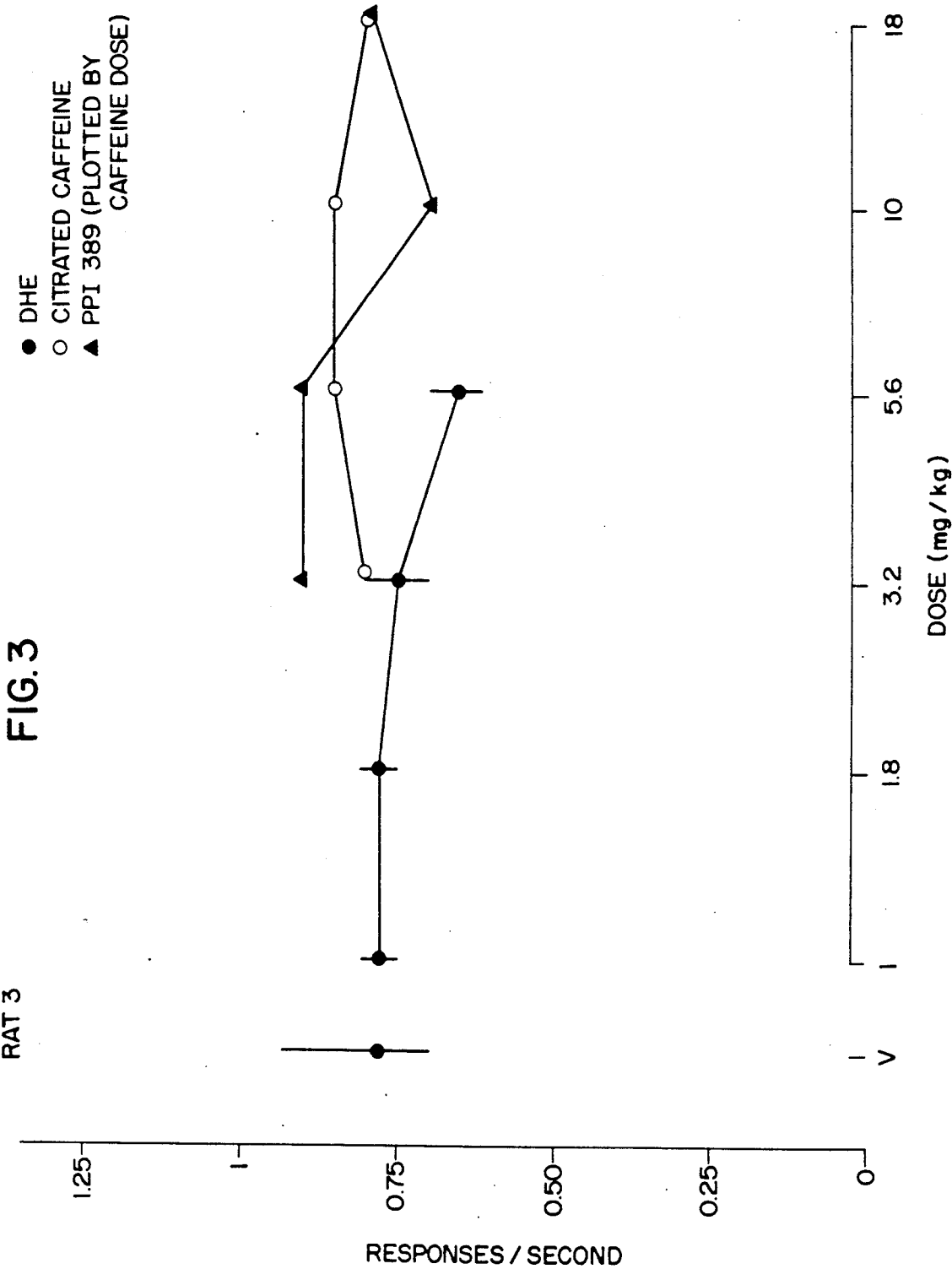
Figure 4:
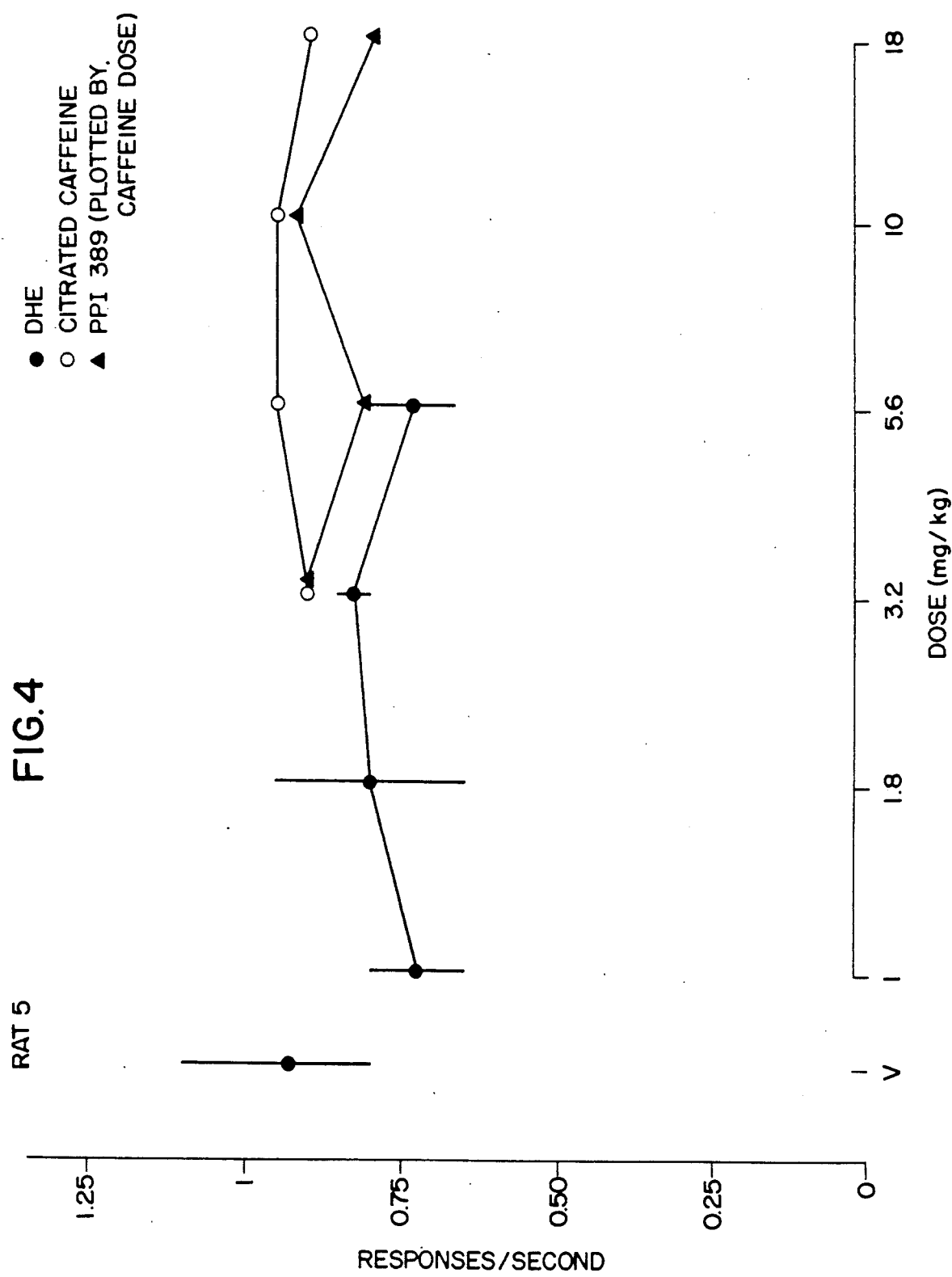
Figure 5:
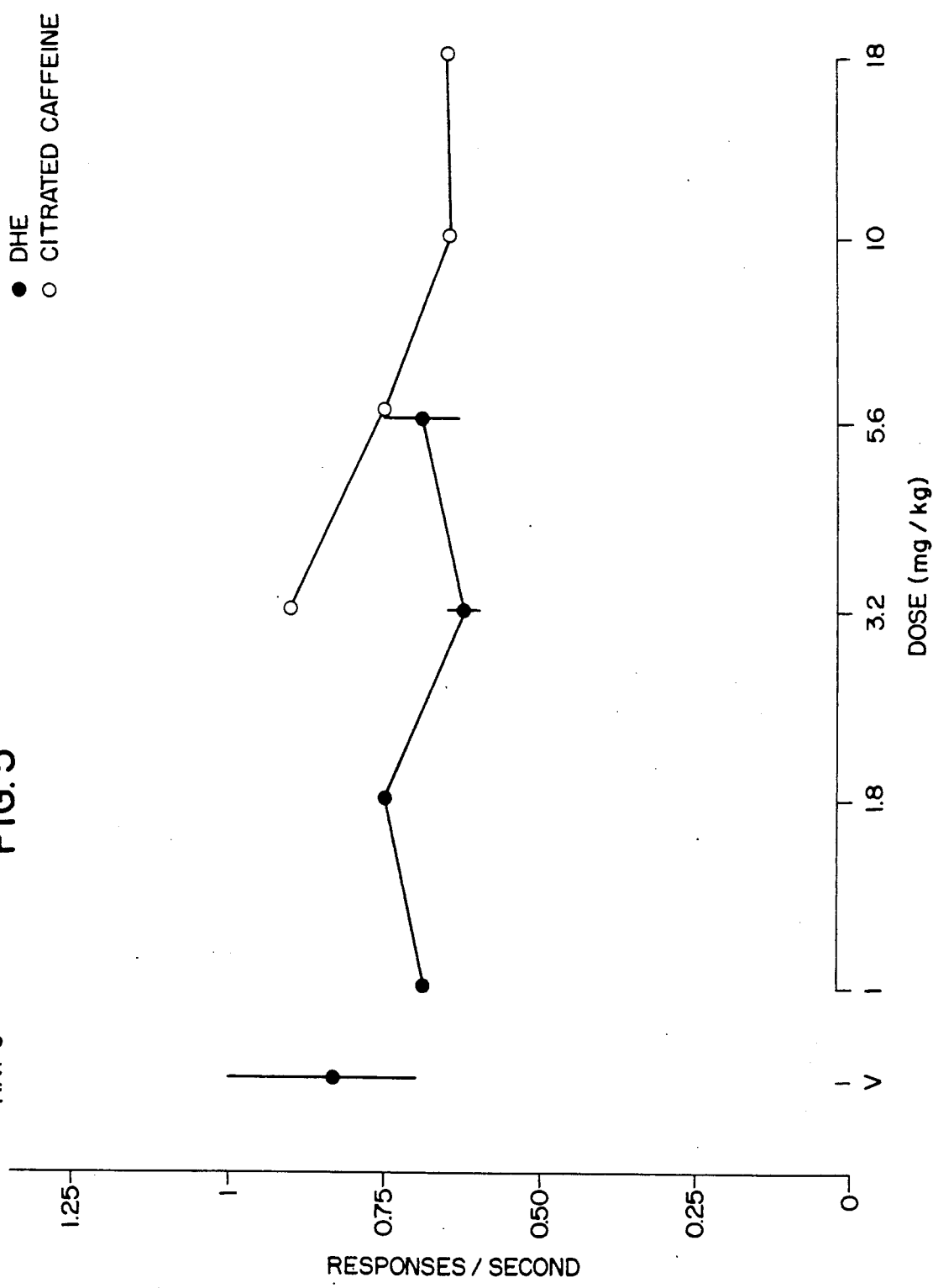

As can be seen in FIGS. 1 through 5, dose-response curves plotted for the above experiment, DHE, caffeine, and PPI 389 produced only small (if any) dose-related decreases in rate of responding at the doses tested.

EXAMPLE 2

An injectable formulation of 4 mg/ml DHE mesylate and 8 mg/ml caffeine citrate was prepared in sterile water. One ml of the composition is administered via intravenous injection daily for four weeks, to an individual who is moderately to severely dependent on cocaine. The dose is reduced by about 20% every two weeks until all physiological and psychic withdrawal symptoms subside.

EXAMPLE 3

The administration regimen of Example 2 is used to deliver an injectable formulation of 4 mg/ml DHE mesylate and 8 mg/ml caffeine citrate to an individual who is addicted to amphetamines. Again, the dose is reduced by about 20% every two weeks until all physiological and psychic withdrawal symptoms subside.

EXAMPLE 4

The administration regimen of Examples 2 and 3 is used to deliver an injectable formulation of 4 mg/ml DHE mesylate and 8 mg/ml caffeine citrate to an individual who is addicted to nicotine. Again, the dose is reduced by about 20% every two weeks until all physiological and psychic withdrawal symptoms subside.

EXAMPLE 5

A formulation of 4 mg/ml DHE mesylate and 8 mg/ml caffeine citrate was prepared in a sterile saline solution containing 3 wt.% glycerin, 0.80 wt.% sodium chloride, EDTA, and benzalkonium chloride, buffered to nasal pH. glycerin and sterile saline. One ml of the composition is administered as a nasal spray daily for four weeks, to an individual who is moderately to severely dependent on cocaine. The dose is reduced by about 20% every two weeks until all physiological and psychic withdrawal symptoms subside.

EXAMPLE 6

The administration regimen of Example 5 is used to deliver 4 mg/ml DHE mesylate and 8 mg/ml caffeine citrate to an individual who is addicted to nicotine. Again, the dose is reduced by about 20% every two weeks until all physiological and psychic withdrawal symptoms subside.

EXAMPLE 7

The administration regimen of Examples 5 and 6 is used to deliver 4 mg/ml DHE mesylate and 8 mg/ml caffeine citrate to an individual who is addicted to heroin. Again, the dose is reduced by about 20% every two weeks until all physiological and psychic withdrawal symptoms subside.

I claim:

1. A method for the treatment of a drug-dependent individual, which method comprises administering a therapeutically effective amount of (a) a serotonin antagonist selected from the group consisting of ergotamine, ergotamine derivatives, and pharmacologically acceptable salts thereof; and (b) a CNS stimulant selected from the group consisting of xanthine, xanthine derivatives, and pharmacologically acceptable salts thereof.

2. The method of claim 1 wherein said serotonin antagonist and said CNS stimulant are administered separately.

3. The method of claim 1 wherein said serotonin antagonist and said CNS stimulant are administered simultaneously.

4. The method of claim 3 wherein said serotonin antagonist and said CNS stimulant are administered in a single composition.

5. The method of claim 4 wherein said serotonin antagonist is selected from the group consisting of dihydroergotamine and pharmacologically acceptable salts thereof.

6. The method of claim 5 wherein said serotonin antagonist is dihydroergotamine mesylate.

7. The method of claim 4 wherein said CNS stimulant has the structural formula

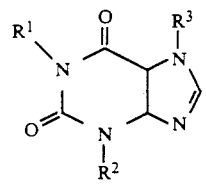

wherein $R^1$, $R^2$ and $R^3$ are independently selected from the group consisting of hydrogen and lower alkyl, and also includes pharmacologically acceptable salts thereof.

8. The method of claim 7 wherein said CNS stimulant is caffeine or a pharmacologically acceptable salt thereof.

9. The method of claim 8 wherein said CNS stimulant is caffeine citrate.

10. The method of claim 5 wherein said CNS stimulant has the structural formula

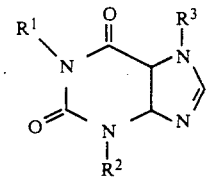

wherein $R^1$, $R^2$ and $R^3$ are independently selected from the group consisting of hydrogen and lower alkyl, and also includes pharmacologically acceptable salts thereof.

11. The method of claim 10 wherein said CNS stimulant is caffeine or a pharmacologically acceptable salt thereof.

12. The method of claim 11 wherein said CNS stimulant is caffeine citrate.

13. The method of claim 6 wherein said CNS stimulant has the structural formula

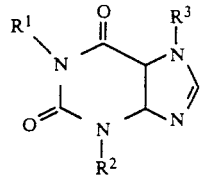

wherein R¹, R² and R³ are independently selected from the group consisting of hydrogen and lower alkyl, and also includes pharmacologically acceptable salts thereof.

14. The method of claim 13 wherein said CNS stimulant is caffeine or a pharmacologically acceptable salt thereof.

15. The method of claim 14 wherein said CNS stimulant is caffeine citrate.

16. The method of claim 4 wherein said composition is administered at least once in every 24 hours in a unit dose.

17. The method of claim 16 wherein said unit dose comprises in the range of about 1 to 10 mg serotonin antagonist and 2 to 12 mg CNS stimulant.

18. The method of claim 4 wherein said composition is administered by injection.

19. The method of claim 18 wherein said injection is subcutaneous, intramuscular or intravenous.

20. The method of claim 4 wherein said composition is administered orally.

21. The method of claim 4 wherein said composition is administered transdermally.

22. The method of claim 4 wherein said composition is administered transmucosally.

23. The method of claim 4 wherein said composition is administered rectally.

24. The method of claim 4 wherein said composition is administered periodically throughout the duration of a treatment period.

25. The method of claim 1, wherein the drug-dependent individual is addicted to a narcotic.

26. The method of claim 1, wherein the drug-dependent individual is addicted to cocaine.

27. The method of claim 1, wherein the drug-dependent individual is addicted to amphetamines.

28. The method of claim 1, wherein the drug-dependent individual is addicted to nicotine.

29. A method for the treatment of a drug-dependent individual, which method comprises administering daily a composition comprising:
(a) 2 to 6 mg dihydroergotamine or a pharmacologically acceptable salt thereof; and
(b) 6 to 10 mg caffeine or a pharmacologically acceptable salt thereof.

* * * * *